US008828967B2

(12) United States Patent
Autuori et al.

(10) Patent No.: US 8,828,967 B2

(45) Date of Patent: Sep. 9, 2014

(54) LOW MOLECULAR WEIGHT COMPLEXES BETWEEN IRON AND MALTOBIONIC ACID, USE THEREOF FOR INTRAMUSCULAR OR SUBCUTANEOUS ADMINISTRATION IN THE TREATMENT OF ANEMIC STATES, AND NEW PHARMACEUTICAL COMPOSITIONS ADAPTED FOR THESE USES

(75) Inventors: Michele Autuori, Modena (IT); Dario Bosi, Reggiolo (IT); Alessandro Lapini Sacchetti, Modena (IT); Egidio Marchi, Casalecchio di Reno (IT)

(73) Assignee: Biofer S.p.A. (IT)

( * ) Notice: Subject to any disclaimer, the term of this patent is extended or adjusted under 35 U.S.C. 154(b) by 0 days.

(21) Appl. No.: 13/703,111

(22) PCT Filed: Jun. 8, 2011

(86) PCT No.: PCT/EP2011/059498
§ 371 (c)(1), (2), (4) Date: Dec. 10, 2012

(87) PCT Pub. No.: WO2011/154452
PCT Pub. Date: Dec. 15, 2011

(65) Prior Publication Data

US 2013/0079298 A1 Mar. 28, 2013

(30) Foreign Application Priority Data

Jun. 9, 2010 (IT) .............................. MI2010A1028

(51) Int. Cl.

| | |
|---|---|
| ***A01N 43/04*** | (2006.01) |
| ***A61K 31/715*** | (2006.01) |
| ***C07H 15/04*** | (2006.01) |
| ***C07H 23/00*** | (2006.01) |

(52) U.S. Cl.
CPC .................................... *C07H 23/00* (2013.01); *C07H 15/04* (2013.01)
USPC ..... 514/53; 536/121; 536/123.1; 536/123.13; 560/121; 560/122

(58) Field of Classification Search
None
See application file for complete search history.

(56) References Cited

FOREIGN PATENT DOCUMENTS

| | | | |
|---|---|---|---|
| WO | 2005000210 | A2 | 1/2005 |
| WO | 2006111802 | A1 | 10/2006 |
| WO | 2007081744 | A2 | 7/2007 |

OTHER PUBLICATIONS

International Search Report; International Application No. PCT/EP2011/059498; International Filing Date Jun. 8, 2011; Mail date Sep. 9, 2011.
Written Opinion; International Application No. PCT/EP2011/059498; International Filing Date Jun. 8, 2011; Mail date Sep. 9, 2011.
International Preliminary Report on Patentability; International Application No. PCT/EP2011/059498; International Filing Date Jun. 8, 2011; Mail date May 21, 2011.
Reply to Written Opinion of the ISA dated Sep. 9, 2011 for corresponding International Application No. PCT/EP2011/059498; International Filing Date Jun. 8, 2011.

*Primary Examiner* — Patrick Lewis
(74) *Attorney, Agent, or Firm* — Cantor Colburn LLP

(57) ABSTRACT

New low molecular weight complexes between iron and maltobionic acid that can be administered parenterally, preferably intramuscularly or subcutaneously, in the treatment of anemic states, caused by iron deficiencies, and new pharmaceutical compositions adapted for this use. In particular, the invention provides a new complex between preferably trivalent iron and maltobionic acid that is characterized by a molecular weight Mw between 10,000 and 30,000 Da, by a polydispersity of 1.0-1.8 and by an iron content between 25% and 40% by weight.

18 Claims, 9 Drawing Sheets

$^{13}C$ Example (I.5) in $D_2O$ $^{13}C$ Ferinject Batch: 916200 in $D_2O$

Program Version :<6,2> Sample name : Example (15) Operator :Biofer
Sample number :155

Numerical average (Mn) : 10603 Weight average (Mw) : 14683
Polydispersity (Mw/Mn) : 1.385 Total area : 2.4672101e+007 (microvolt seconds)

Program version :<6.2> Sample name :Ferinject Vifor 916206 Operator :Biofer
Sample number :154

Numerical average (Mn) : 68302 Weight average (Mw) : 182202
Polydispersity (Mw/Mn) : 2.668 Total area : 2.3572161e+007 (microvolt seconds)

LOW MOLECULAR WEIGHT COMPLEXES BETWEEN IRON AND MALTOBIONIC ACID, USE THEREOF FOR INTRAMUSCULAR OR SUBCUTANEOUS ADMINISTRATION IN THE TREATMENT OF ANEMIC STATES, AND NEW PHARMACEUTICAL COMPOSITIONS ADAPTED FOR THESE USES

TECHNICAL FIELD

The present invention relates to new low molecular weight complexes between iron and maltobionic acid that can be administered parenterally, preferably intramuscularly or subcutaneously, in the treatment of anemic states, caused by iron deficiencies, and to new pharmaceutical compositions adapted for this use.

BACKGROUND ART

One of the essential elements for the growth, development and support of the vital functions of the body is iron. Iron is essential for hemoglobin synthesis and has a positive influence on the erythrocyte count and on the hematocrit value. Iron deficiency in the body causes states of anemia, a disorder that occurs frequently in patients of all ages.

Iron deficiency can also be treated orally, although this method often yields only a partial success due to the modest absorption of the trivalent iron or to the serious side effects (*Blood,* 1955, 10 35-45 “Acute intestinal Iron Intoxication I” and *Blood,* 1955, 10 46-51 “Acute intestinal Iron Intoxication II”); these effects occur following the administration of divalent or trivalent iron salts such as ferrous sulfate, ferrous ammonium sulfate, iron gluconate, ferrous succinate, ferrous fumarate, ferric-sorbitol-citrate complex, ferric sulfate, ferric succinate, ferric fumarate, ferric ammonium oxalate, et cetera.

Oral administration of iron salts, especially for extended periods or at high doses, is hardly feasible due to the risks linked to the gastric tolerability of divalent iron salts and to a risk of overdose due to the high absorption of said salts; for trivalent iron salts, instead, there is a tolerability and low absorption problem.

Accordingly, oral administration of iron is difficult to manage, even if theoretically it is easier and less expensive than parenteral administration, especially intravenous administration.

Therefore, the intravenous parenteral approach, despite having administration problems and being usually performed in a hospital or day hospital, is preferable due to certainty of absorption and, therefore, to documentable effectiveness.

Currently, for practical use, the physician has at his disposal a large number of preparations on the market, with considerable relative differences in their chemical, physical and pharmaceutical peculiarities. According to traditional classification, which is based solely on chemical peculiarities (A. Müller, Arzneim. Forsch., 24 (6), 880883 (1974)), all anti-anemic remedies are classified in four basic groups: iron salts, iron chelates with low molecular weight, sandwich complexes with low molecular weight and polynuclear complexes of ferric hydroxide with carbohydrates. In the treatment of anemias caused by iron deficit, the latter, i.e., parenteral preparations based on polynuclear complexes of ferric hydroxide, have proved themselves to be the most effective.

In order to administer these complexes, the most widespread parenteral approach is the intravenous one (iv). For this type of administration, preparations must have some particular chemical-physical and biological characteristics, such as good iron bioavailability correlated to the type of complex and to its chemical stability. Moreover, it is necessary to guarantee a lack of local or general side effects, such as anaphylactic shock or hepatic toxicity linked to the impurities derived from the breakdown of sugar, to the molecular weight of the complex and to the free iron contained in the compound.

Accordingly, the chemical-physical characteristics of the complex are closely tied to the type of sugar used, to the content of iron bonded in the complex, and to the molecular weight. All these characteristics also affect directly the stability and the bioavailability of the complex. Among the most widespread complexes of iron with carbohydrates authorized for intravenous administration there is, for example, iron dextran with high molecular weight (about 265 kD) marketed under the trademark Dexferrum®, iron dextran with low molecular weight (about 165 kD) marketed under the trademarks Cosmofer® and Pharmacosmos®, iron gluconate with a molecular weight lower than 50 kD and marketed under the trademark Ferlecit®, iron saccharate with a molecular weight comprised between 34-60 kD, marketed under the trademark Venofer® and iron carboxy-maltodextrin with a molecular weight higher than 100 kD, known as Ferinject® in Europe and as Injectafer□™ in the United States, where however it is still in the process of being approved by the FDA. The active ingredient of Ferinject®/Injectafer™□, i.e., a polynuclear complex between trivalent iron and activated maltodextrins (“VIT-45”) with a molecular weight comprised between 100,000 and 350,000 daltons, particularly 150,000 daltons, and its intravenous and intramuscular use are disclosed in WO 2007/081744. It should be noted that despite the fact that VIT-45 has been named “ferric carboxymaltose” by the USAN Council (a US national body that assigns ordinary names to new drugs, similar to the international nonproprietary names “INN” issued by the WHO), see http://www.ama-assn.org/ama1/pub/upload/mm/365/ferric_carboxymaltos.pdf, this definition actually is not suitable from a chemical point of view, because VIT-45 is obtained from pure maltodextrins with a DE of 5-20, or from mixtures of maltodextrins with a DE of 5-40, while maltose is a disaccharide, and therefore by definition has a DE of 50. The most appropriate name for VIT-45 would be, therefore, iron carboxy-maltodextrin.

Despite this very wide context, from the medical point of view an improvement is still needed because, according to Gasche et al. in Inflamm. Bowel Dis. 13 (12) 1545-1551 (12/2007), all these preparations in any case have specific peculiarities and limitations (see also Geisser et al. Arzneimittelforschung 42, Nr. 12 (1992) 1439-1452). From a clinical point of view, existing products may be divided into the following categories:

1) Fe-gluconate: intravenous and/or oral administration in some countries. This is a complex classified as type III based on the strength of the sugar-iron bond, which is defined as labile and weak, and therefore iron release occurs entirely over 4-6 hours.

2) Fe-saccharate: administered only intravenously with a pH of 10.5-11. This is a complex classified as type II because it is more stable than the previous one. The iron is released over the 8-12 hours that follow administration.

3) Fe-polymaltose: administered intravenously or intramuscularly. This is a complex classified as type I due to the particular stability of the iron-maltodextrin bond. The iron is released, therefore, over the 36 hours that follow administration and therefore it does not have immediate bioavailability.

4) Fe-dextran: administered intravenously. This is a complex classified as type I for the remarkable stability of the iron-dextran bond, which affects heavily the release of the iron, which occurs over the 72-96 hours that follow administration.

It is useful, in any case, to remember that among the ones described above, the preparations mainly used in treatment today are still the historically older ones, i.e., iron saccharate and iron-dextran, even though both have considerable risks for toxicity, which is due mainly to the adverse reactions, of the anaphylactoid type for dextran (Hamstra et al., "Intravenous Iron Dextran in Clinical Medicine" JAMA, 1980, 243, 17 1726-1732) and of acute toxicity for iron saccharate, due to the presence of labile iron and impurities (Zager et al., "Parenteral iron formulations: A comparative toxicologic analysis and mechanisms of cell injury." Am. J. Kid. Dis., 2002, 40, 1, 90-103).

It should be noted that intramuscular application (by infusion or injection) of products that have physiologically acceptable pH values of the solutions is suitable only for hospital use, due to the high risk caused by side effects. For Ferinject® (VIT-45), the information leaflet (issued to licensee Syner-Med and indicating as owner of the AIM (marketing authorization) Vifor France SA) indicates only the intravenous path as usable, and states explicitly that the intramuscular administration path is not allowed, contradicting what was stated in WO 2007/081744.

Therefore, it is important to note that the products authorized for intramuscular administration are currently very few—and that with these products important side effects often occur due to the inherent characteristics of the complex or due to the type of intramuscular administration, for example infusion or bolus injection.

Moreover, to the extent of the Applicant's knowledge, even today there are no products on the market that are authorized for subcutaneous administration.

This leads to the need to have available, in the treatment of anemic states due to iron deficiency, new active ingredients/products that allow simple administration, intramuscularly and/or optionally also subcutaneously, and also allow home use and not only hospital use.

DISCLOSURE OF THE INVENTION

The Applicant has now found surprisingly that this aim and these and other aims that will become better apparent hereinafter are achieved by new low molecular weight complexes between iron and maltobionic acid, characterized by a molecular weight (MW) between 10,000 and 30,000 Da, by a polydispersity of 1.0-1.8 and by an iron content between 25% and 40% by weight (w/w). Further aspects of the invention are the development of new pharmaceutical formulations that comprise the new complexes, adapted for intramuscular or preferably subcutaneous administration.

WAYS OF CARRYING OUT THE INVENTION

Figure 1:
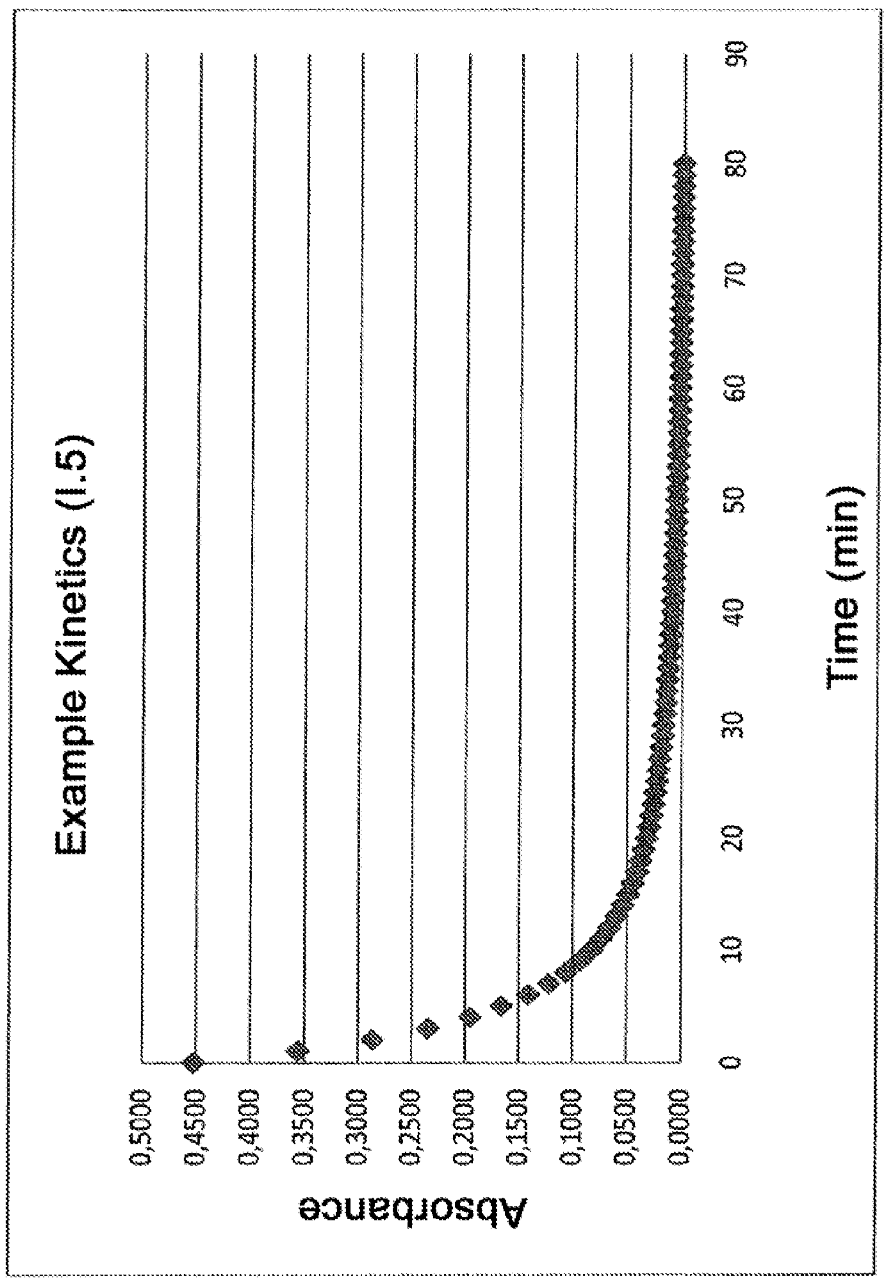
FIG. 1 plots the iron reduction kinetics of a complex according to the invention (see example 1.5).

The complexes between iron and maltobionic acid disclosed by the invention are intended for the treatment of anemias, i.e., of deficiencies of iron and/or hemoglobin and of the associated diseases. In some cases, anemia is caused by iron deficiency, such as anemia associated with chronic or acute loss of blood, pregnancy, childbirth, infant development, psychomotor development, severe uterine hemorrhages, menstruations, recurrent chronic hemoptysis, parasite infections, chronic renal diseases and dialysis, surgical procedures or acute traumas, chronic ingestion of alcohol, or steroids, chronic ingestion of NSA (non-steroidal anti-inflammatory agents) or chronic ingestion of agents that stimulate erythropoiesis. In other cases the anemia may be an anemia associated with other diseases, such as rheumatoid arthritis, cancer, Hodgkin's leukemia, non-Hodgkin leukemia, anti-cancer chemotherapy, inflammatory bowel disease (IBD), ulcerative colitis, thyroiditis, hepatitis, systemic lupus erythematosus, polymyalgia rheumatica, scleroderma, connective tissue diseases, Sojgren's syndrome, congestive heart failure/cardiomyopathy, or idiopathic geriatric anemia. In other cases, the anemia may be due to disorders in iron absorption, inadequate nutrition or undernutrition, such as for example anemias associated with Crohn's disease, gastric surgery, ingestion of drugs that inhibit the absorption of iron or chronic ingestion of calcium. The pathological states that can entail anemic states comprise, among other things, restless leg syndrome (RLS), blood donations, Parkinson's disease, hair loss, or disorders that lead to attention/concentration deficit, to name a few.

The new pharmacological formulations described herein allow the treatment of the disorders described above by intramuscular or subcutaneous administration, particularly by intramuscular injection or subcutaneous injection, in both cases without the appearance of serious adverse reactions.

The Applicant has in fact found surprisingly that low molecular weight complexes between iron and maltobionic acid, particularly complexes between trivalent iron, preferably iron oxide-hydroxide, and maltobionic acid that have a molecular weight (MW) comprised between 10,000 and 30,000 daltons, a polydispersity of 1.0-1.8 and an iron content between 25% and 40% by weight (w/w) are suitable for the purposes indicated above.

This result is unexpected, because, as shown in the general description provided by Gasche et al., the state of the background art is that of a problematic situation, which seems to exclude the possibility to obtain a parenteral preparation of iron oxide-hydroxide, complexed with a sugar that can be used in replacement therapy in concentrated colloidal solutions, that can be administered intramuscularly or even subcutaneously. This result, moreover, also seems to be in contrast with what is known so far about iron complexes used in therapy; in fact, a low molecular weight is associated with a higher toxicity, which can be attributed to a greater presence of labile iron, i.e., of iron easily released into the blood without the intervention of a bond with a specific protein such as transferrin, even though, on the other hand, a complex with low weight should be less allergenic. From the chemical-physical point of view, generally a low weight complex is less stable, so much that it requires, in solution, high pH conditions, i.e., higher than 10.5 in order to keep the molecular weight within the initial values. This fact is very important at the physiological level, because it limits, for these compounds, an exclusively intravenous therapeutic use. This is the case of iron oxide-hydroxide saccharate and iron oxide-hydroxide gluconate. On the other hand, complexes with higher molecular weight, being more stable, can be formulated at a physiological pH, in theory can also be administered intramuscularly and are considered to have low toxicity, although they may cause serious side effects of the allergic type. In practice, they can be used almost exclusively intravenously because the bioavailability of the iron is low, since the iron-sugar bond is very strong, and therefore the iron itself is released very slowly and the complex, if administered intramuscularly, tends to remain in the tissue for a long time, causing tissue damage in addition to allergic reactions.

The present invention relates, therefore, to low molecular weight complexes between trivalent iron, preferably iron oxide-hydroxide and maltobionic acid, that surprisingly combine the possibility to be formulated in physiological pH conditions, preferably with a pH between 6.0 and 8.0, and at high concentrations (up to 200 mg/ml of Fe), at the same time with low allergenicity and low toxicity, making them easy to administer intramuscularly or subcutaneously, preferably in bolus, in therapeutic dosages.

The expression "low molecular weight complexes between iron, preferably iron oxide-hydroxide, and maltobionic acid" is intended to reference complexes between preferably trivalent iron and maltobionic acid that have a molecular weight (MW) comprised between 10,000 and 30,000 daltons, a polydispersity between 1.0 and 1.8, preferably between 1.0 and 1.6, and an iron titer comprised between 25% and 40% by weight. Preferably, the expression "complexes between trivalent iron oxide-hydroxide and maltobionic acid" is intended to reference complexes between trivalent iron oxide-hydroxide and maltose wherein the aldehyde end group of the maltose has been oxidized to a carboxyl group, i.e., a polynuclear complex between iron (III) hydroxide or oxyhydroxide and 4(R)-(1→4)O-α-glucopyranosyl)-oxy-2(R),3(S),5(R),6-tetrahydroxy-hexanoic acid.

Preferably, these complexes are formulated as solutions or aqueous colloidal solutions. The average molecular weight (MW) of these complexes, determined with GPC as per USP 32 with dextran standards, amounts to 10,000-30,000 daltons, preferably 12,000-27,000 daltons, more preferably 13,000-18,000 daltons. The complexes according to the invention preferably demonstrate a high uniformity of the average molecular weight (MW); in fact, the polydispersity calculated as ratio between MW/Mn (parameter provided by monograph USP 32, same method of molecular weight) is comprised between 1.0 and 1.8, more preferably 1.0 and 1.6, more preferably 1.1-1.5 and even more preferably between 1.2 and 1.4. This narrow range of polydispersity not only ensures uniformity of molecular weight, but the inventors have also found that it contributes to guaranteeing and ensuring uniformity in the release of the iron and excludes the presence of labile iron.

The inventors of the present application have also found that the complexes as above may contain up to 50% by weight of Fe (w/w); however, for the practical purposes described herein, and to achieve the advantages of the invention, one must select values of Fe comprised between 25% and 40% by weight, preferably between 25% and 35% by weight, more preferably between 26% and 32% by weight, even more preferably between 26% and 28.5% by weight, most preferably between 26.5% and 28.5% by weight.

Within the scope of the complexes described above, preference is given to complexes characterized by a molecular weight Mw between 12,000 and 27,000 Da, by a polydispersity of 1.0-1.8, preferably 1.0-1.6, more preferably 1.1-1.5, and by an iron content between 25% and 40% by weight, even more preferably characterized by a molecular weight Mw between 13,000 and 18,000 Da, by a polydispersity of 1.2-1.4 and by an iron content between 25% and 40% by weight. Further preferred complexes are characterized by a molecular weight Mw between 13,000 and 18,000 Da, by a polydispersity of 1.2-1.4 and by an iron content between 25% and 35% by weight. Further preferred complexes are characterized by a molecular weight Mw between 12,000 and 27,000 Da, by a polydispersity of 1.1-1.5 and by an iron content between 26% and 32% by weight, even more preferably characterized by a molecular weight Mw between 13,000 and 18,000 Da, by a polydispersity of 1.2-1.4 and by an iron content between 26% and 28.5% by weight, preferably between 26.5% and 28.5% by weight.

The step of oxidation of the maltose described herein may be obtained with the methods described in WO 2006/111802 by the same Applicant, but not in a reproducible manner with other published methods. The method according to WO 2006/111802 is therefore preferred because it provides, as mentioned, a quantitative and selective oxidation of the aldehyde group of the maltose, so as to obtain a product that is absolutely homogeneous and stable, can be purified easily and is therefore adapted for use in the pharmaceutical field. In the method according to WO 2006/111802, the oxidation of the maltose is performed so that the residual reducing capacity of the obtained carboxymaltose is lower than 1%, as easily demonstrable by $^{13}C/^{1}H$ NMR or HPLC. The synthesis of the activated maltose, performed by accurate, specific and quantitative oxidation of the aldehyde group in position C1 of the maltose, provides a sugar with a particular capacity to complex the iron oxide-hydroxide and capable of giving to said complex the characteristics desired and found by the Applicant in the complexes described herein. In fact, the homogeneity of maltobionic acid, i.e., the high purity it has as a chemical reagent, is capable of ensuring the homogeneity and uniformity of the complex, which can be verified easily through a polydispersity that is very close to 1 and above all in an excellent chemical-physical stability. In fact, the perfect homogeneity of the aqueous solution that contains the complex itself, which never tends to precipitate as occurs in other complexes also obtained with disaccharides as occurs for example for Venofer®, as described in the information leaflet, is always demonstrated.

The Applicant has now found that by varying the ratios between activated maltose (preferably with the method described above) and iron oxide-hydroxide, one obtains low molecular weight complexes which are stable at physiological pH.

Therefore, a non-exclusive general synthesis method according to the present invention follows the present pattern of four steps:

(i) "activation", i.e., specific oxidation of maltose to give maltobionic acid, (ii) complexation of the maltobionic acid with ferric oxide-hydroxide generated in solution, (iii) purification of the complex between ferric oxide-hydroxide and maltobionic acid, not yet stabilized, (iv) stabilization of the complex between ferric oxide-hydroxide and maltobionic acid.

From the stabilization (iv), after cooling, one obtains an alkaline solution (pH 9-12, for example 11±0.5) that contains the active ingredient in the form of iron oxide-hydroxide and maltobionic acid. This solution can be used in order to prepare the pharmaceutical solutions to which the present invention relates, neutralizing/buffering the solution to physiological pH and then optionally adding suitable excipients, all followed by a suitable sterilization treatment (for example, 0.22 micron filtration). As an alternative, from the solution obtained from step (iv) as above it is possible to isolate the complex in the form of dry solid powder, for example as described in WO 2006/111802 (by freeze-drying or spray drier). The powder thus obtained can then be used in turn for preparing various pharmaceutical forms suitable for intramuscular or subcutaneous or intravenous administration. Among these, firstly, physiological solutions similar to those obtained directly from the solution as in (iv), but other forms as well. The complexes of the invention in dry solid form can also be formulated unmodified or with the addition of suitable solid excipients for the (re)constitution of a physiological solution that can be injected at the time of use, by adding a suitable diluent. Formulations that can be reconstituted may also be obtained from said injectable formulations, for example by freeze-drying them before packaging.

The formulation of the complexes as described above is feasible, since the inventors of the present application have found that these complexes are soluble and stable in aqueous environments at physiological pH without further stabilization by adding sugars or other stabilizers, which would modify some chemical-physical characteristics such as osmolality, viscosity, solubility.

EXAMPLES

Example (I.1)

Comparative 0.5 g of sodium bromide are added to 50.0 g of maltose dissolved in 167 ml of purified water and the pH of the resulting solution is corrected between 7.5 and 8.5 with sodium hydroxide. Then 88.21 g of sodium hypochlorite with 11.74% of active chlorine are added to the mixture. This addition must occur slowly (over a period of 2 hours), keeping the pH between 7.0 and 9.0 with sodium hydroxide. The added hypochlorite corresponds to the stoichiometric quantity for total oxidation of the aldehyde end group of the maltose to carboxylic acid.

At the end of the addition the solution is kept under agitation for 30 minutes, during which the total oxidation of the aldehyde end group is verified by virtue of the HPLC method.

188.10 g of a ferric chloride solution at 38.60% w/w are added to the activated maltose solution, and the mixture is cooled to 17.0° C.±0.5° C.

Once the indicated temperature has been reached, the pH of the solution is brought to a value of 2.5±0.5 by dripping, in not less than 3 hours, a sodium carbonate solution at 14% w/w. Once this pH value has been reached, the solution is kept under agitation at the temperature of 17.0° C.±0.5° C. for 30 minutes, by correcting the pH to 2.5±0.5, if necessary, always with the sodium carbonate solution at 14% w/w.

The pH is thus brought, in not less than 1 hour, to the value of 10.5±0.5 by addition of sodium hydroxide at 15% w/w.

The solution thus obtained is purified by ultrafiltration by using a filtration system provided with a membrane with a 5000 Da cut-off.

The solution, purified of the salts, is brought to pH 11.0±0.5 and to a temperature of 75° C. for 2.5 hours.

Once the thermal treatment has ended, the solution is cooled and after correction of the pH to 7.0±1.0 with acetic acid it is filtered in a sterile manner.

The complex is isolated by freeze-drying.

The average molecular weight and the polydispersity of the product are determined by using the Gel-Permeation Chromatography (GPC) method, described in the United States Pharmacopoeia (USP) 32$^{nd}$ ed., which provides for two columns in series (TOSO HAAS TSK-GEL G5000PWXL 30 cm×7.8 cm ID+TOSO HAAS TSK-GEL 2500PWXL 30 cm×7.8 cm ID) and dextrans with known molecular weight as standard: 4440, 9890, 21400, 43500, 66700, 123500, 196300, 276500 Da, values taken at the top of the peak (Mp).

The chemical-physical characteristics of the complex are as follows:

Average molecular weight (Mw)=33012

Polydispersity=1.54

$Fe^{3+}$=30.4% w/w

Example (I.2)

Invention 0.5 g of sodium bromide are added to 50.0 g of maltose dissolved in 167 ml of purified water, and the pH of the resulting solution is corrected between 7.5 and 8.5 with sodium hydroxide. Then 88.21 g of sodium hypochlorite with 11.74% of active chlorine are added to the mixture. This addition must occur slowly (over a period of 2 hours), keeping the pH between 7.0 and 9.0 with sodium hydroxide. The added hypochlorite corresponds to the stoichiometric quantity for total oxidation of the aldehyde end group of maltose to carboxylic acid.

At the end of the addition, the solution is kept under agitation for 30 minutes, during which total oxidation of the aldehyde end group is verified by virtue of an HPLC method.

171.00 g of a ferric chloride solution at 38.60% w/w are added to the activated maltose solution and the mixture is cooled to 17.0° C.±0.5° C.

Once the indicated temperature has been reached, the pH of the solution is brought to a value of 2.5±0.5 by dripping, in not less than 3 hours, a sodium carbonate solution at 14% w/w. Once this pH value has been reached, the solution is kept under agitation at the temperature of 17.0° C.±0.5° C. for 30 minutes, correcting the pH to 2.5±0.5, if necessary, always with the sodium carbonate solution at 14% w/w.

The pH is thus brought, in not less than 1 hour, to the value of 10.5±0.5 by addition of sodium hydroxide at 15% w/w. The solution thus obtained is purified by ultrafiltration by using a filtration system provided with a membrane with a 5000 Da cut-off.

The solution purified of the salts is brought to pH 11.0±0.5 and to a temperature of 75° C. for 2.5 hours.

Once the thermal treatment has ended, the solution is cooled and after pH correction to 7.0±1.0 with acetic acid it is filtered in a sterile manner. The complex is isolated by freeze-drying.

The average molecular weight and the polydispersity of the product are determined by using the Gel-Permeation Chromatography (GPC) method, described in the United States Pharmacopoeia (USP) 32$^{nd}$ ed., which has two columns in series (TOSO HAAS TSK-GEL G5000PWXL 30 cm×7.8 cm ID+TOSO HAAS TSK-GEL 2500PWXL 30 cm×7.8 cm ID) and dextrans with known molecular weight as standard: 4440, 9890, 21400, 43500, 66700, 123500, 196300, 276500 Da, values taken at the top of the peak (Mp).

The chemical-physical characteristics of the complex are as follows:

Average molecular weight (Mw)=25441

Polydispersity=1.53

$Fe^{3+}$=30.5% w/w

Example (I.3)

Invention 0.5 g of sodium bromide are added to 50.0 g of maltose dissolved in 167 ml of purified water, and the pH of the resulting solution is corrected between 7.5 and 8.5 with sodium hydroxide. Then 91.03 g of sodium hypochlorite with 11.38% of active chlorine are added to the mixture. This addition must occur slowly (over a period of 2 hours) keeping the pH between 7.0 and 9.0 with sodium hydroxide. The added hypochlorite corresponds to the stoichiometric quantity for the total oxidation of the aldehyde end group of the maltose to carboxylic acid.

At the end of the addition, the solution is kept under agitation for 30 minutes, during which total oxidation of the aldehyde end group is verified by virtue of the HPLC method.

149.16 g of a ferric chloride solution at 38.94% w/w are added to the activated maltose solution and the mixture is cooled to 17.0° C.±0.5° C.

Once the indicated temperature has been reached, the pH of the solution is brought to a value of 2.5±0.5 by dripping, in not less than 3 hours, a sodium carbonate solution at 14% w/w. Once this pH value has been reached, the solution is kept under agitation at the temperature of 17.0° C.±0.5° C. for 30 minutes, correcting the pH to 2.5±0.5, if necessary, always with the sodium carbonate solution at 14% w/w.

The pH is then brought, in not less than 1 hour, to the value of 10.5±0.5 by addition of sodium hydroxide at 15% w/w.

The solution thus obtained is purified by ultrafiltration by using a filtration system provided with a membrane with a 5000 Da cut-off.

The solution purified of the salts is brought to pH 11.0±0.5 and to a temperature of 75° C. for 2.5 hours.

Once the thermal treatment has ended, the solution is cooled and after pH correction to 7.0±1.0 with acetic acid it is filtered in a sterile manner.

The complex is isolated by freeze-drying.

The average molecular weight and the polydispersity of the product are determined using the Gel-Permeation Chromatography (GPC) method, described in the United States Pharmacopoeia (USP) $32^{nd}$ ed., which provides for two columns in series (TOSO HAAS TSK-GEL G5000PWXL 30 cm×7.8 cm ID+TOSO HAAS TSK-GEL 2500PWXL 30 cm×7.8 cm ID) and dextrans with a known molecular weight as standard: 4440, 9890, 21400, 43500, 66700, 123500, 196300, 276500 Da, values taken at the top of the peak (Mp).

The chemical-physical characteristics of the complex are as follows:

Average molecular weight (Mw)=14479

Polydispersity=1.37

$Fe^{3+}$=26.1% w/w

Example (I.4)

Invention 0.5 g of sodium bromide are added to 50.0 g of maltose dissolved in 167 ml of purified water and the pH of the resulting solution is corrected between 7.5 and 8.5 with sodium hydroxide. Then 75.81 g of sodium hypochlorite with 13.66% of active chlorine are added to the mixture. This addition must occur slowly (over a period of 2 hours) keeping the pH between 7.0 and 9.0 with sodium hydroxide. The added hypochlorite corresponds to the stoichiometric quantity for the total oxidation of the aldehyde end group of the maltose to carboxylic acid. At the end of the addition, the solution is kept under agitation for 30 minutes, during which the total oxidation of the aldehyde end group is verified by virtue of the HPLC method.

123.13 g of a ferric chloride solution at 39.31% w/w are added to the activated maltose solution and the mixture is cooled to 17.0° C.±0.5° C.

Once the indicated temperature has been reached, the pH of the solution is brought to a value of 2.5±0.5 by dripping, in not less than 3 hours, a sodium carbonate solution at 14% w/w. Once this pH value has been reached, the solution is kept under agitation at the temperature of 17.0° C.±0.5° C. for 30 minutes, correcting the pH to 2.5±0.5, if necessary, always with the sodium carbonate solution at 14% w/w.

The pH is then brought, in not less than 1 hour, to the value of 10.5±0.5 by addition of sodium hydroxide at 15% w/w.

The solution thus obtained is purified by ultrafiltration by using a filtration system provided with a membrane with a 5000 Da cut-off.

The solution purified of the salts is brought to pH 11.0±0.5 and to a temperature of 75° C. for 2.5 hours.

Once the thermal treatment has ended, the solution is cooled and after pH correction to 7.0±1.0 with acetic acid is filtered in a sterile manner. The complex is isolated by freeze-drying.

The average molecular weight and the polydispersity of the product are determined by using the Gel-Permeation Chromatography (GPC) method, described in the United States Pharmacopoeia (USP) $32^{nd}$ ed., which has two columns in series (TOSO HAAS TSK-GEL G5000PWXL 30 cm×7.8 cm ID+TOSO HAAS TSK-GEL 2500PWXL 30 cm×7.8 cm ID) and dextrans with known molecular weight as standard: 4440, 9890, 21400, 43500, 66700, 123500, 196300, 276500 Da, values taken at the top of the peak (Mp).

The chemical-physical characteristics of the complex are as follows:

Average molecular weight (Mw)=12272

Polydispersity=1.27

$Fe^{3+}$=25.4% w/w

Example (I.5)

Invention (Industrial Scale)

0.14 kg of sodium bromide are added to 14.0 kg of maltose dissolved in 47 l of purified water, and the pH of the resulting solution is corrected between 7.5 and 8.5 with sodium hydroxide. Then 22.25 kg of sodium hypochlorite with 13.03% w/w of active chlorine are added to the mixture. This addition must occur slowly (over a period of 2 hours) keeping the pH between 7.0 and 9.0 with sodium hydroxide. The added hypochlorite corresponds to the stoichiometric quantity for the total oxidation of the aldehyde end group of the maltose to carboxylic acid.

At the end of the addition, the solution is kept under agitation for 30 minutes, during which the total oxidation of the aldehyde end group is verified by virtue of the HPLC method.

37.87 kg of a ferric chloride solution at 42.95% w/w are added to the activated maltose solution and the mixture is cooled to 17.0° C.±0.5° C.

Once the indicated temperature has been reached, the pH of the solution is brought to a value of 2.5±0.5 by dripping, in not less than 3 hours, a sodium carbonate solution at 14% w/w. Once this pH value has been reached, the solution is kept under agitation at the temperature of 17.0° C.±0.5° C. for 30 minutes, correcting the pH to 2.5±0.5, if necessary, always with the sodium carbonate solution at 14% w/w.

The pH is then brought, in not less than 1 hour, to the value of 10.5±0.5 by addition of sodium hydroxide at 15% w/w.

The solution thus obtained is purified by ultrafiltration, using a filtration system provided with a membrane with a 5000 Da cut-off.

The solution purified of the salts is brought to pH 11.0±0.5 and to a temperature of 75° C. for 2.5 hours.

Once the thermal treatment has ended, the solution is cooled and after pH correction to 7.0±1.0 with acetic acid is filtered in a sterile manner. The complex is isolated by freeze-drying.

The average molecular weight and the polydispersity of the product are determined by using the Gel-Permeation Chromatography (GPC) method, described in the United States Pharmacopoeia (USP) 32$^{nd}$ ed., which has two columns in series (TOSO HAAS TSK-GEL G5000PWXL 30 cm×7.8 cm ID+TOSO HAAS TSK-GEL 2500PWXL 30 cm×7.8 cm ID) and dextrans with known molecular weight as standard: 4440, 9890, 21400, 43500, 66700, 123500, 196300, 276500 Da, values taken at the top of the peak (Mp).

The chemical-physical characteristics of the complex are as follows:

Average molecular weight (Mw)=14683
Polydispersity=1.38
$Fe^{3+}$=27.4% w/w

Example (I.6)

Comparative (Example 3 as per WO 2006/111802)

60 grams of maltose are dissolved in 200 ml of purified water, 0.6 g of sodium bromide are added, and the pH of the solution is correct to a value between 7.0 and 9.0 with a sodium hydroxide aqueous solution. Over two hours, 98.5 g of 12% active sodium hypochlorite are added, corresponding to the stoichiometric quantity with respect to the aldehyde end groups, keeping the pH value between 7.0 and 9.0.

At the end of the addition, the solution is kept under agitation for 30 minutes, during which the accomplished total aldehyde end group oxidation is assessed by HPLC, detecting the ratio between residual maltose and activated maltose.

257 g of a 40% wt FeC13 solution (iron/sugar ratio=1:1.7 w/w) are added to the activated maltose solution, brought to a temperature between 16° C. and 20° C., continuing the agitation until complete homogenization of the reaction mixture occurs. Then a 15% w/v solution of Na2CO3 is added to the resulting solution slowly over 3 hours, so as to bring the pH to a value between 2.3 and 2.7. Once this value has been reached, the solution is kept under agitation and in these conditions for 15 minutes, checking that the pH value remains between 2.3 and 2.7, and then the pH value is brought to 10.5±0.5 over 1 hour, by adding a 15% w/v sodium hydroxide solution. No precipitation of iron hydroxide is required, not even in the form of a complex.

The solution thus obtained is purified by ultrafiltration by using a filtration system provided with a membrane with a 3000 Da cut-off.

The solution purified of the salts is brought to a pH 11.5±0.5 and heated to 75° C.±2° C. for a period of 2 hours. At the end of the heating, the complex is cooled and isolated by freeze-drying.

The physical-chemical features of the complex are as follows:

Average molecular weight (Mw)=53655 Daltons*
Numerical molecular weight (Mn)=35988 Daltons*
Polydispersity=1.5
Content in $Fe^{3+}$ 41.4%.

*The molecular weights have been determined using the method according to page 1065 of the United States Pharmacopeia (USP), 28$^{th}$ ed.

Example (II.1)

Formulation at 50 mg/ml of Iron 4500 ml of water for injection (90% of the final volume of solution) are loaded into a 5-liter flask. 930.7 g of powder iron complex with a Fe titer equal to 27.4% w/w o.d.b. and an R.S. equal to 98.03% (example I.5) are added to the water in small amounts under agitation. The mixture is left under agitation up to complete dissolution of the solid. After 15 minutes of agitation, the pH of the solution is then corrected to 7.0 with the addition of acetic acid at 40% w/w. The solution thus obtained is transferred into a graduated 5-liter flat-bottom flask, the dissolution flask is rinsed with water for injection up to complete removal of the red colored solution, adding the rinses to the rest of the solution. The volume of the solution is thus brought to 5 liters exactly in the graduated flat-bottom flask, always with water for injections. Optionally, before bringing the solution to volume, excipients suitable for the parenteral formulations may also be added. The solution thus obtained, after analytic control of the iron titer (50 mg/ml, i.e., 5% w/v of iron) may be used, after sterilizing filtration, for the preparation of the following pharmaceutical dosage forms:

vials;
vials with ring cap;
pre-filled syringe vials.

Example (III.1)

Comparison with Ferinject®

TABLE I

| | Parameters | Ferinject ® (Vifor) Batch 916200 | Invention |
|---|---|---|---|
| 1 | Complexing sugar | Activated maltodextrins | Activated maltose |
| 2 | Molecular weight | Stated in WO 2007/081744: 90,000-350,000 Da, specifically 150,000 Da<br>Found: approx. 200,000 Da (Mw)-(in actual fact 182,202 Da (Mw)) | Claimed 10,000 Da-30,000 Da (Mw)<br>Tested: 14,683 Da (Mw) |
| 3 | Poly-dispersity | Found approx. 2.67 (in actual fact 2.668) | Claimed: 1.0-1.8<br>Tested approx. 1.38 |

TABLE I-continued

| | Parameters | Ferinject ® (Vifor) Batch 916200 | Invention |
|---|---|---|---|
| | | | (in actual fact 1.385) |
| 4 | % Fe (weight/weight) | Stated in WO 2007/081744: 10-40% (preferably 20-35%) Found = 27.5% | Claimed 25-40% Tested 27.4% |
| 5 | Turbidity point | Absent | Absent |
| 6 | Iron reduction kinetics | Stated in WO 2007/081744: 117.8 mins Found: 196 mins | Found: 7-8 mins |

Commentaries:

Item 3: polydispersity=ratio between Mw and Mn

Item 5: in order to determine the turbidity point, the USP method reported in the Iron Sucrose monograph was performed. The absence of a turbidity point is to be associated, for both products, with a low iron content in the complex (less than 28% by weight in both cases).

Item 6: the method used for the study of reduction kinetics is reported in U.S. Pat. No. 6,911,342. For the complex according to the invention, T75 (time needed for 75% reduction of the initial Fe) is 7-8 mins (see FIG. 1), while for Ferinject® it is longer: the method would prescribe recording for 80 minutes, but it was chosen to continue recording absorbance up to 5 hours.

Figure 2:
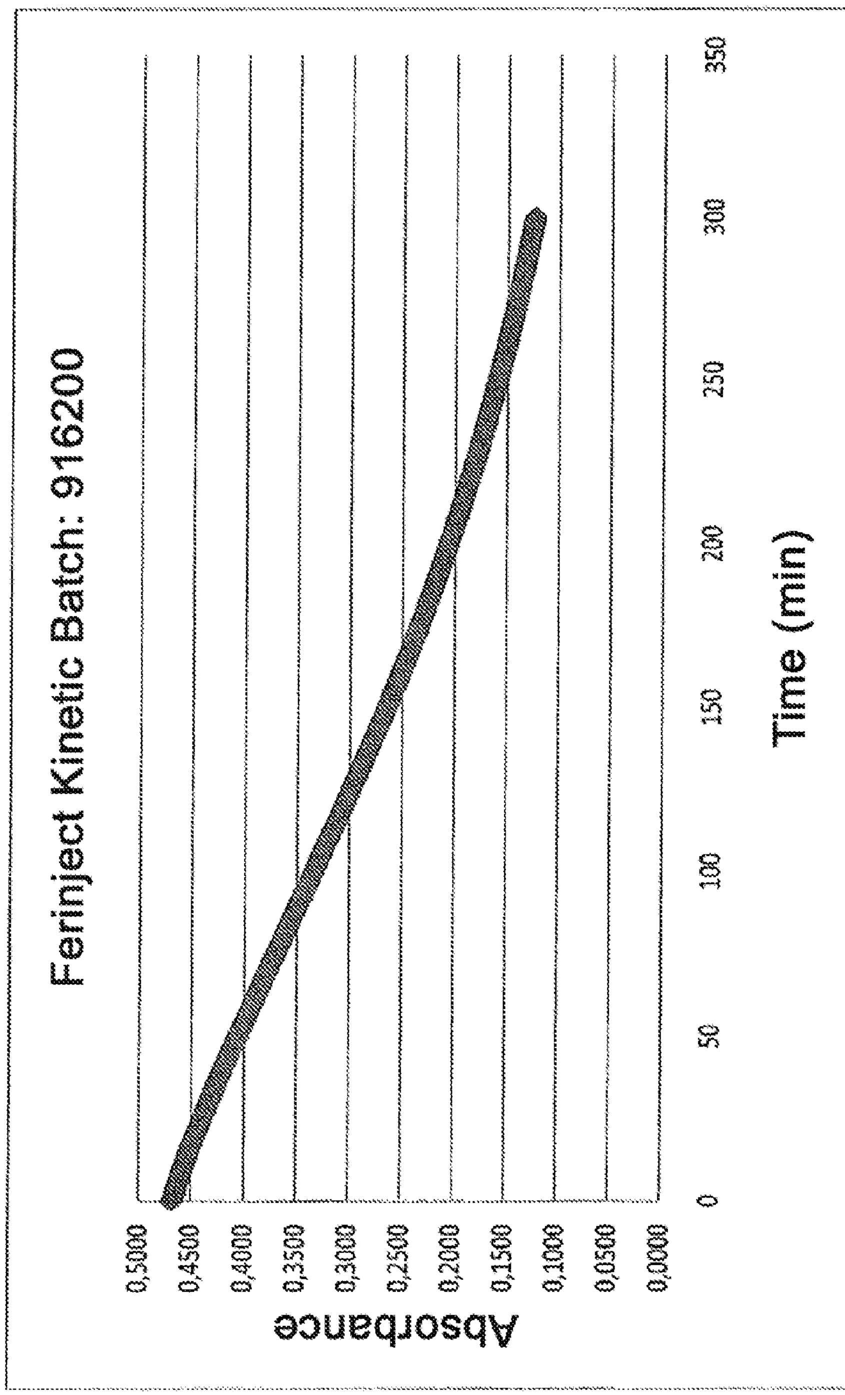
FIG. 2 plots the iron reduction kinetics of Ferinject®.
Figure 3:
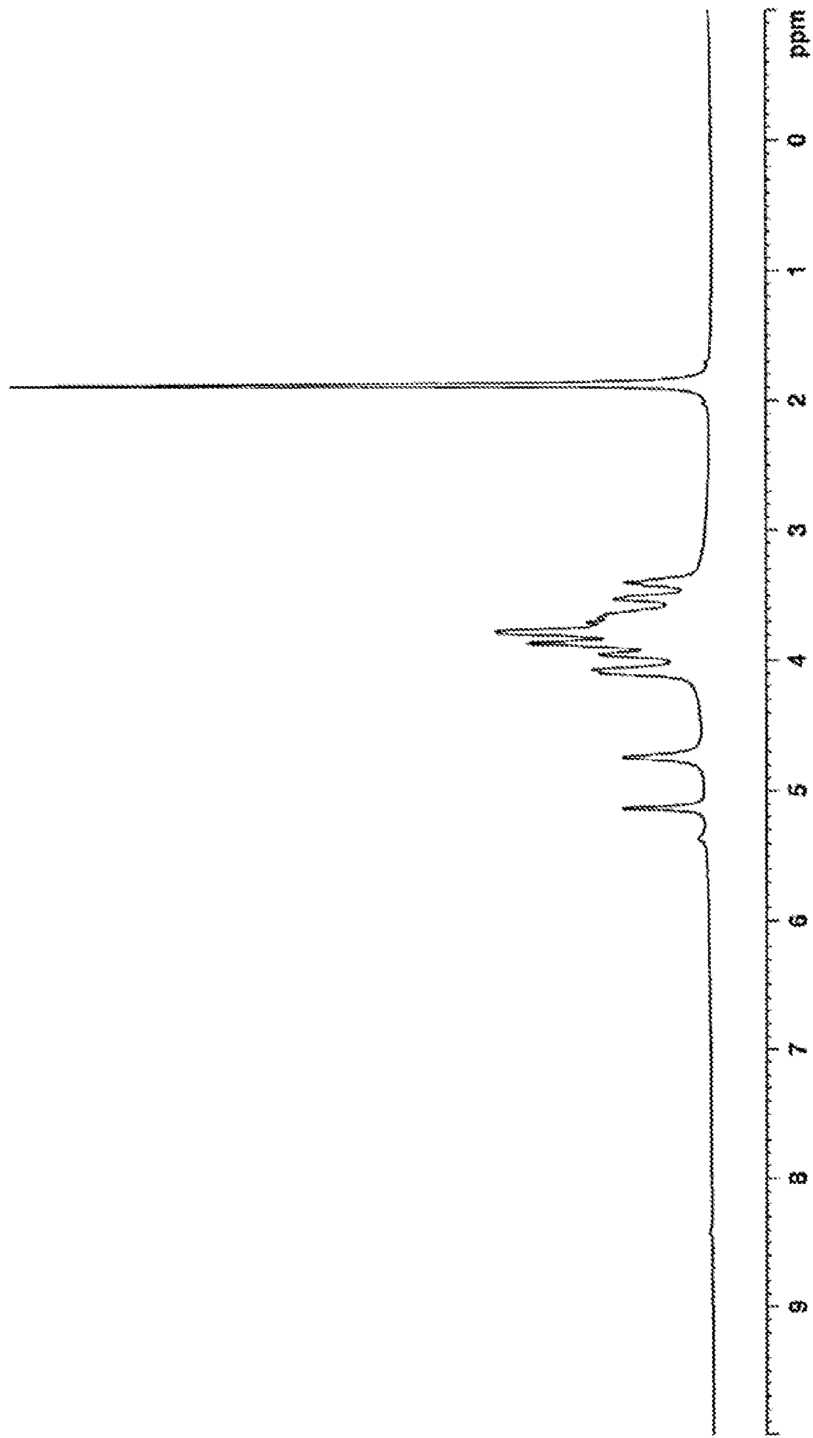
FIG. 3 plots the $^{1}$H NMR spectrum of a complex according to the present invention (see example 1.5).
Figure 4:
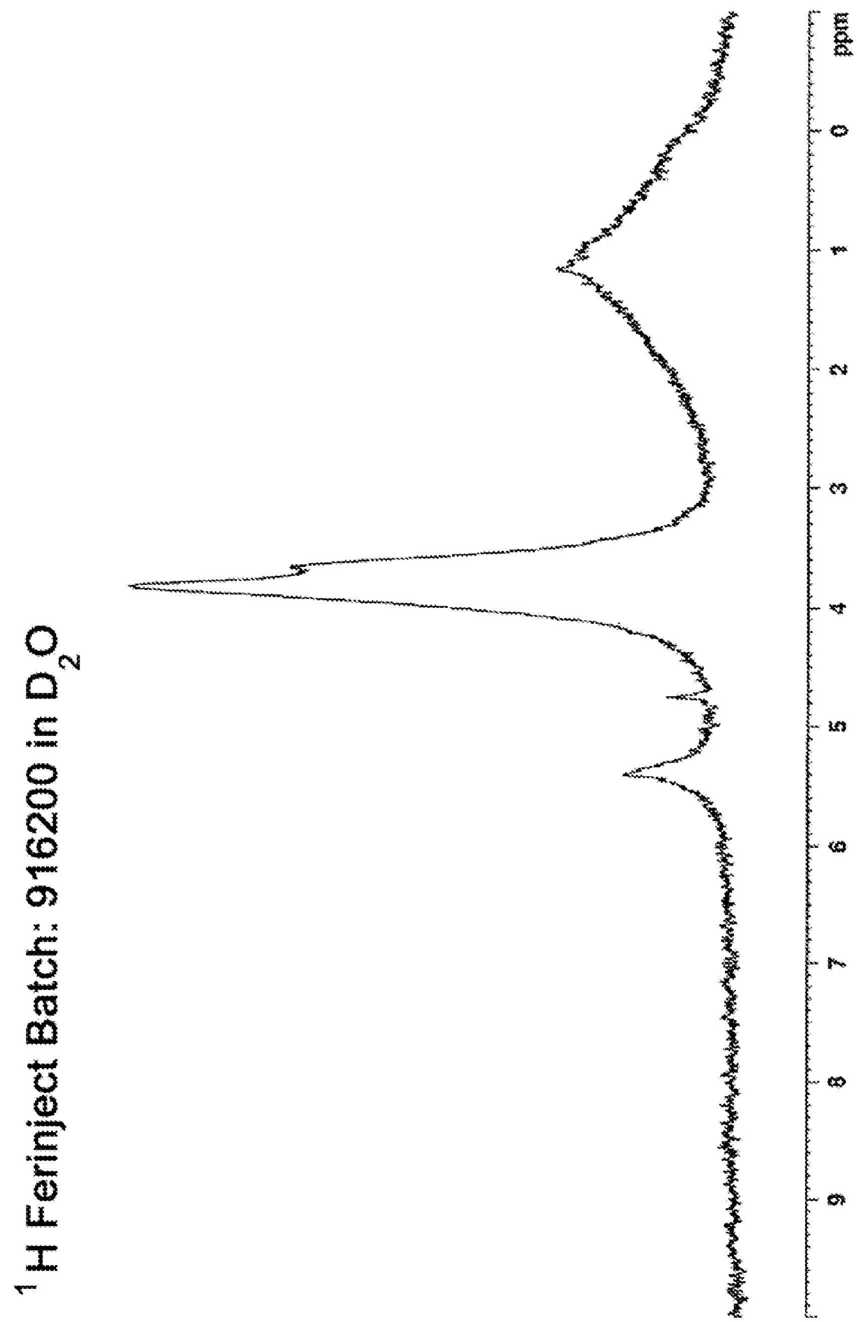
FIG. 4 plots the $^{1}$H NMR spectrum of Ferinject®.
Figure 5:
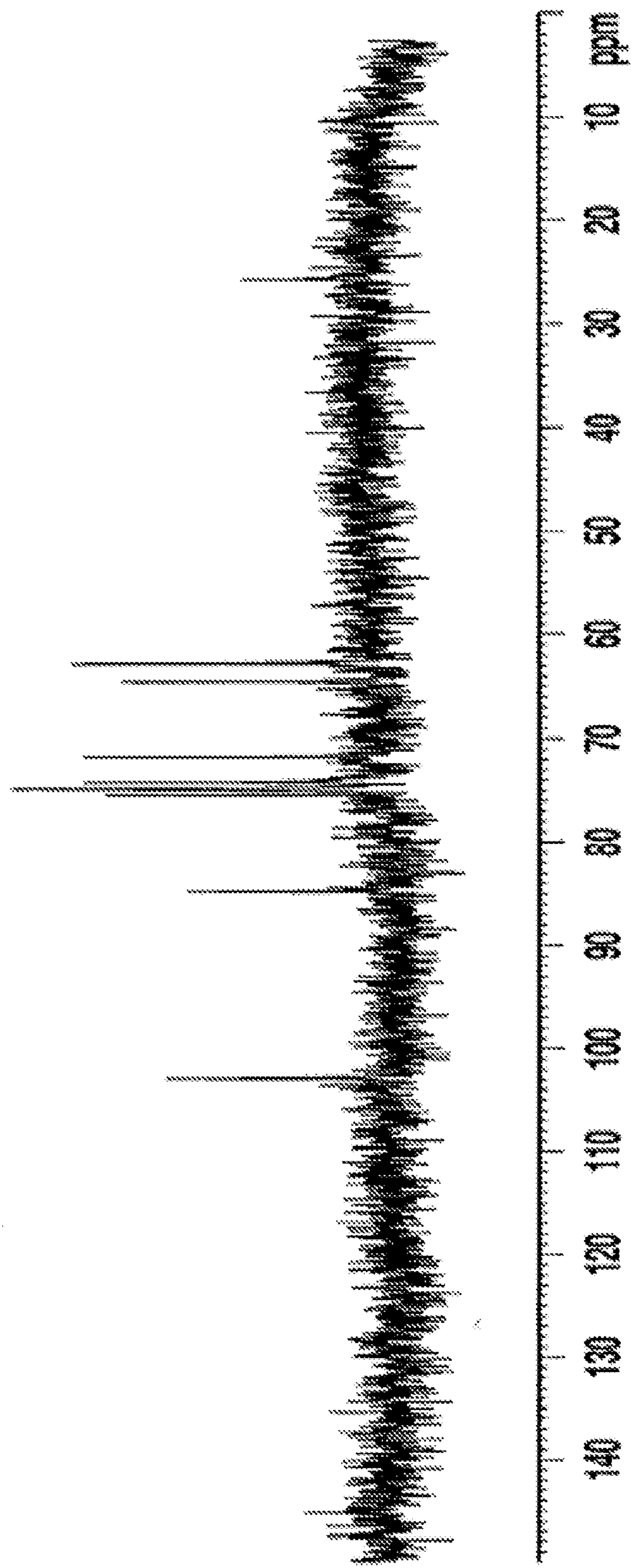
FIG. 5 plots the $^{13}$C NMR spectrum of a complex according to the present invention (see example 1.5).
Figure 6:
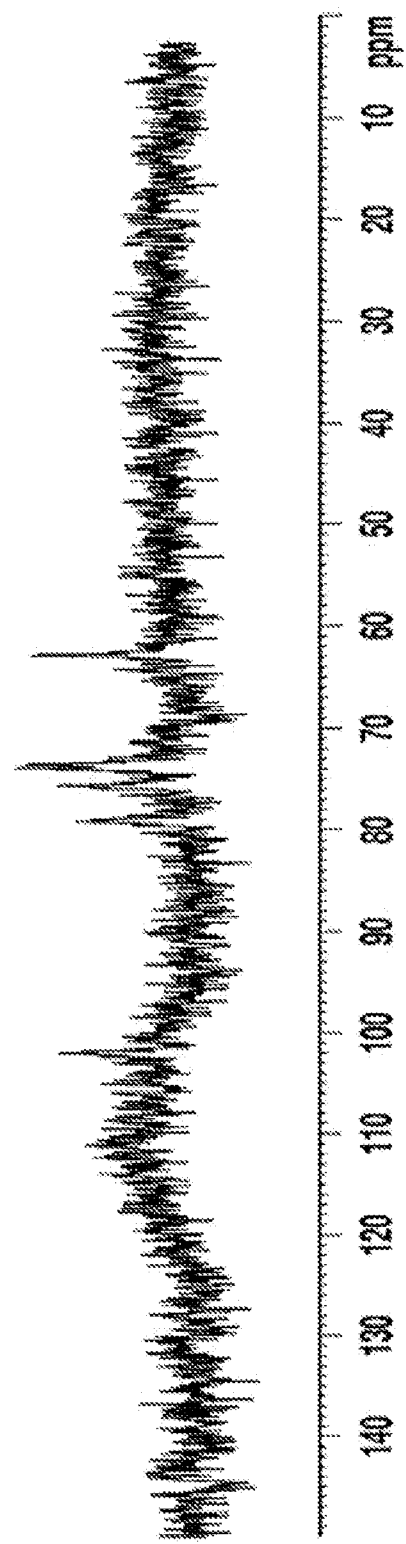
FIG. 6 plots the $^{13}$C NMR spectrum of Ferinject®.
Figure 7:
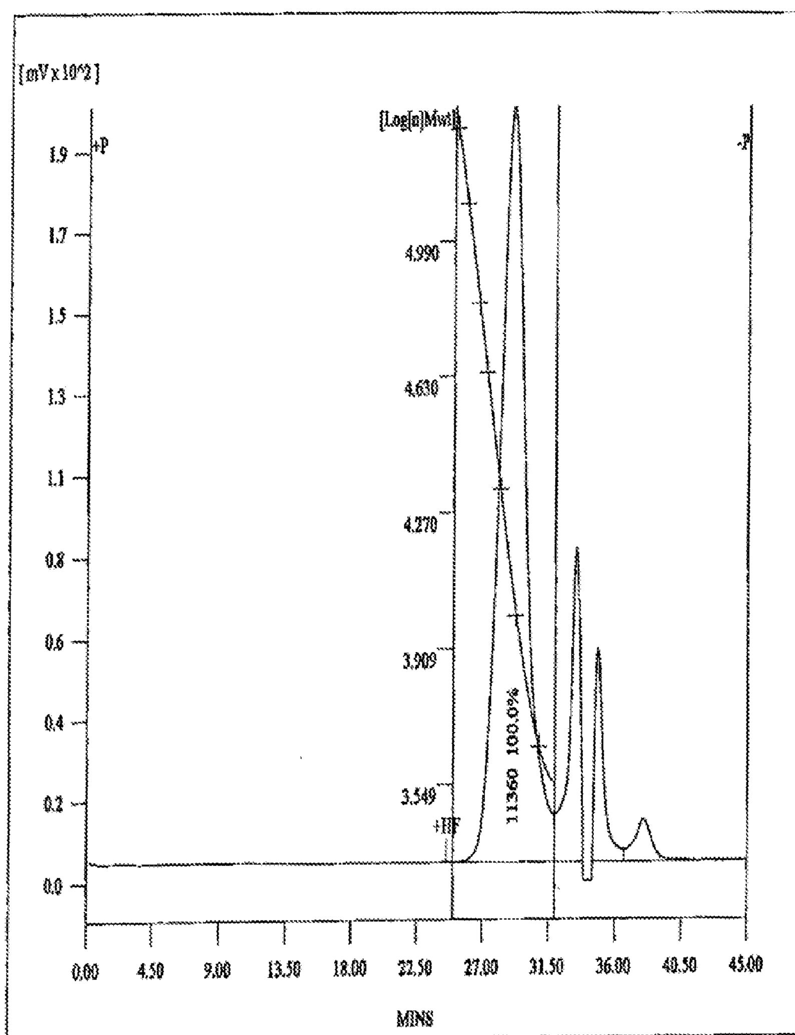
FIG. 7 is an HPLC (GPC) chromatogram of a complex according to the present invention (see example 1.5).
Figure 8:
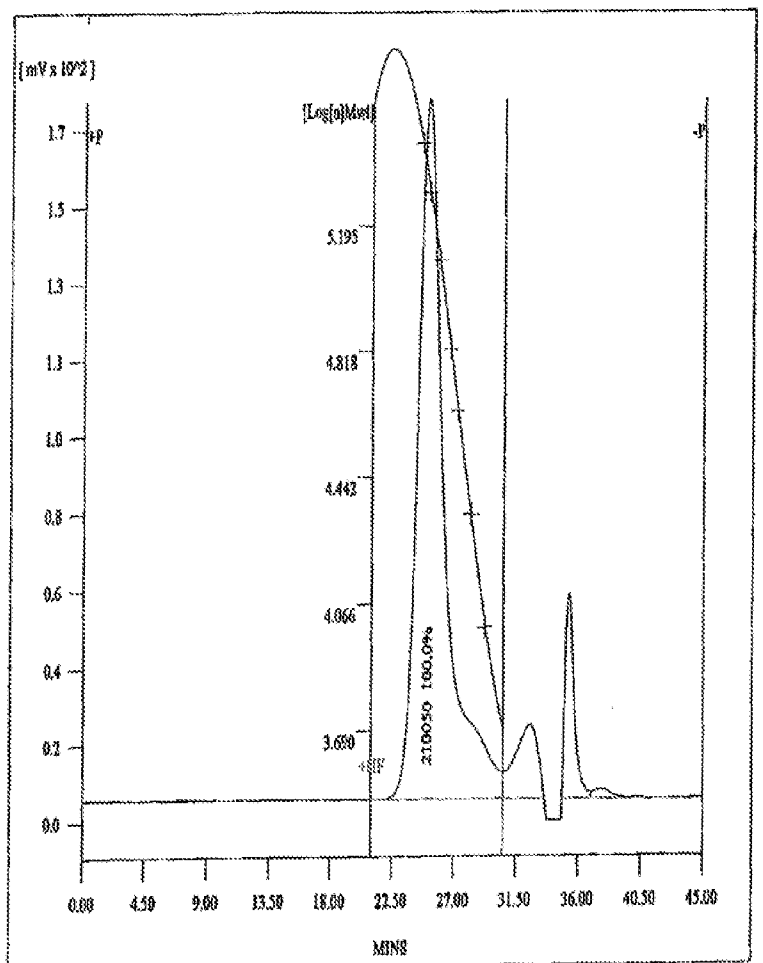
FIG. 8 is an HPLC (GPC) chromatogram of Ferinject®.

In any case, even after this time, all the iron is not reduced, because the absorbance does not reach zero. According to WO 2007/081744, the T75 of Ferinject® is 117.8 mins (however, total recording time is not indicated); for a 5-hour recording, the T75 determined by the Applicant is equal to 196 minutes (see FIG. 2).

Example (IV)

Pharmacological Testing (IV.1) Pharmacokinetics.

Pharmacokinetic tests were run with the complex as per example 1.3 of the invention. The complex was tested in hogs of about 30 kg weight (selected because of ease of administration) upon intramuscular (i.m.) and subcutaneous (s.c.) bolus administration. The dose administered was 1.67 mg Fe/kg (as a model for a therapeutic dosage of 100 mg Fe to be administered to a female patient of 60 kg). For both types of administration (i.m. and s.c.) plasma samples were drawn after certain time intervals, evaluating both, total Fe and Fe bound to transferrin. For determining total Fe, hog plasma was tested colorimetrically according to the iron-ferene method (Kit no. 0089 by Giesse Diagnostics). For determining transferrin-bound Fe, hog plasma was tested colorimetrically with Kit no. 0022 and Kit no. 0089 by Giesse Diagnostics.

Figure 9:
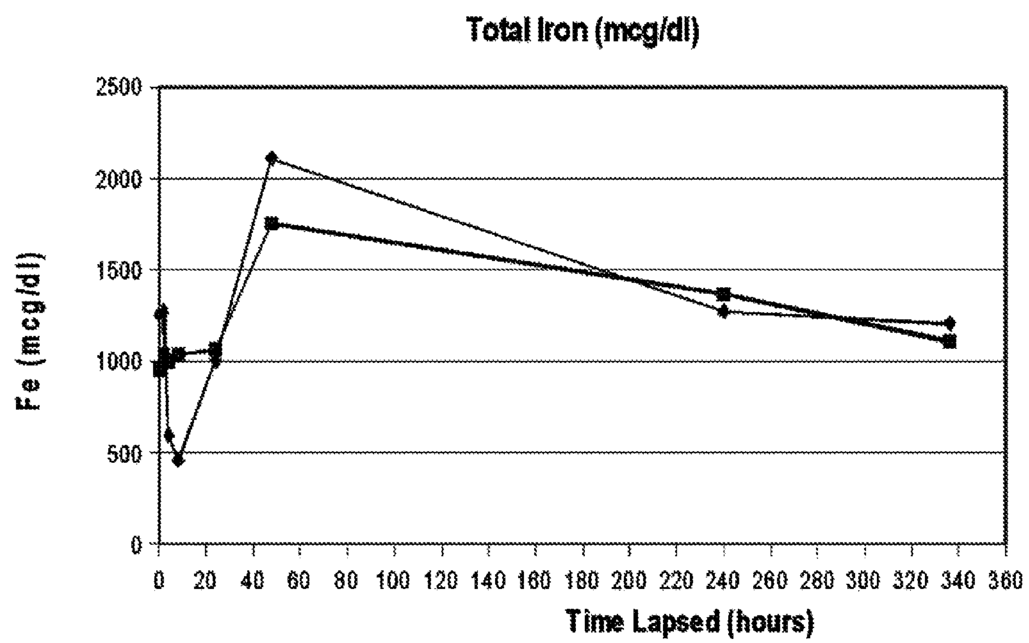
FIG. 9 shows total iron content in hog plasma, as produced by the absorption of a complex according to the present invention (see example I.3) administered by i.m. and s.c. bolus to the hogs.
Figure 10:
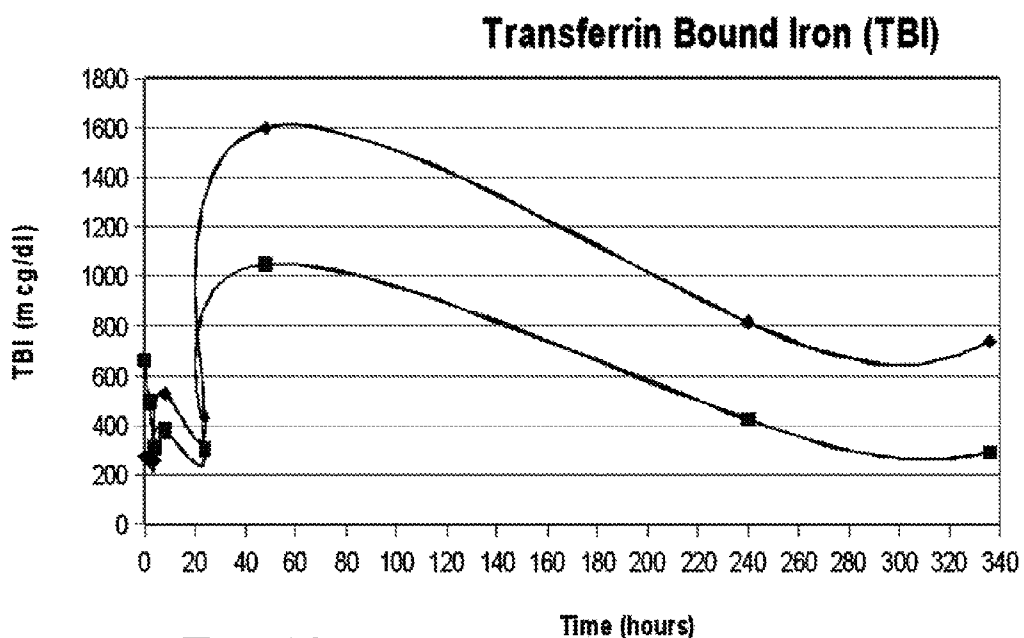
FIG. 10 shows transferrin-bound iron content in hog plasma, as produced by the absorption of a complex according to the present invention (see example 1.3) administered by i.m. and s.c. bolus to the hogs.

The results obtained (see Tables II and III below, as well as FIGS. 9 and 10) did show successful absorption for both, i.m. bolus and s.c. bolus administration, with a peak at about 48 hours post injection. The diamonds in FIGS. 9 and 10 show the absorption curves for i.m. absorption, whereas the squares in FIGS. 9 and 10 show the absorption curves for s.c. absorption.

TABLE II

| | Description samples | Vol reactive | Vol. Water | Vol sample/std | Dil | E Sample | E Blank sample | E std | E Blank std | Fe (mcg/dl) |
|---|---|---|---|---|---|---|---|---|---|---|
| | Reactive blank | 900 | 200 | | | | | | | |
| | | | Vol reactive (per dilution) | | | | | | | |
| | Fe (100 mcg/dl) | 900 | | 200 | | | | 0.11 | 0.02 | |
| 0 | 29 T0 I.M. | 900 | 150 | 50 | 4 | 0.3313 | 0.0429 | 0.1069 | 0.0151 | 1257 |
| 2 | T2 I.M. | 900 | 150 | 50 | 4 | 0.3090 | 0.0169 | 0.1069 | 0.0151 | 1273 |
| 4 | T4 I.M. | 900 | 150 | 50 | 4 | 0.1390 | 0.0023 | 0.1069 | 0.0151 | 596 |
| 8 | T8 I.M. | 900 | 150 | 50 | 4 | 0.1363 | 0.0310 | 0.1069 | 0.0151 | 459 |
| 24 | 30 T24 I.M. | 900 | 150 | 50 | 4 | 0.2487 | 0.0176 | 0.1069 | 0.0151 | 1007 |
| 48 | 06/07 48 h | 900 | 150 | 50 | 4 | 0.5247 | 0.0401 | 0.1069 | 0.0151 | 2112 |
| 240 | 09/07 10 days I M. | 900 | 150 | 50 | 4 | 0.3005 | 0.0083 | 0.1069 | 0.0151 | 1273 |
| 336 | 13/7 14 days I.M. | 900 | 150 | 50 | 4 | 0.2849 | 0.0077 | 0.1069 | 0.0151 | 1208 |
| | Fe (100 mcg/dl) | 900 | | 200 | | | | 0.11 | 0.0138 | |
| 0 | 29 T0 SC | 900 | 150 | 50 | 4 | 0.2592 | 0.0390 | 0.1054 | 0.0138 | 962 |
| 2 | 29 T2 SC | 900 | 150 | 50 | 4 | 0.2852 | 0.0476 | 0.1054 | 0.0138 | 1038 |
| 4 | 29 T4 SC | 900 | 150 | 50 | 4 | 0.2397 | 0.0104 | 0.1054 | 0.0138 | 1001 |
| 8 | 29 T8 SC | 900 | 150 | 50 | 4 | 0.2553 | 0.0181 | 0.1054 | 0.0138 | 1036 |
| 24 | 30 T24 SC | 900 | 150 | 50 | 4 | 0.2657 | 0.0219 | 0.1054 | 0.0138 | 1065 |
| 48 | 06/07 48 h SC | 900 | 150 | 50 | 4 | 0.4180 | 0.0165 | 0.1054 | 0.0138 | 1753 |
| 240 | 09/07 10 days SC | 900 | 150 | 50 | 4 | 0.3357 | 0.0222 | 0.1054 | 0.0138 | 1369 |
| 336 | 13/7 14 days S.C. | 900 | 150 | 50 | 4 | 0.2607 | 0.0063 | 0.1054 | 0.0138 | 1111 |
| | Normal control serum lot 8088 | 900 | | 200 | 1 | 0.1230 | 0.0167 | 0.1054 | 0.0138 | 101 |
| | Pathological ctrl, serum lot 3163 | 900 | | 200 | 1 | 0.1924 | 0.0135 | 0.1054 | 0.0138 | 170 |

Specification of control sera for both, tables II and III: 89-131 μg/dl Fe (normal); 139-200 μg/dl Fe (pathological).

TABLE III

| | Description samples | Vol reactive | Vol water | Vol sample/std | Dil | E Sample | E Blank sample | E std | E Blank std | Fe (mcg/dl) |
|---|---|---|---|---|---|---|---|---|---|---|
| | Reactive blank | 900 | 200 | | | | | | | |
| | Fe (100 mcg/dl) | 900 | | 200 | | | | 0.0920 | 0.0130 | |
| 0 | 29 T0 I.M. | 900 | | 200 | 3 | 0.0854 | 0.0134 | 0.0920 | 0.0130 | 273 |
| 2 | T2 I.M. | 900 | | 200 | 3 | 0.0747 | 0.0062 | 0.0920 | 0.0130 | 260 |
| 4 | T4 I.M. | 900 | | 200 | 3 | 0.0761 | 0.0083 | 0.0920 | 0.0130 | 257 |
| 8 | T8 I.M. | 900 | | 200 | 3 | 0.1545 | 0.0160 | 0.0920 | 0.0130 | 526 |
| 24 | 30 T24 I.M. | 900 | | 200 | 3 | 0.1574 | 0.0438 | 0.0920 | 0.0130 | 431 |
| 48 | 06/07 48 h | 900 | | 200 | 3 | 0.4700 | 0.0492 | 0.0920 | 0.0130 | 1598 |
| 240 | 09/07 10 days I.M. | 900 | | 200 | 3 | 0.2322 | 0.0177 | 0.0920 | 0.0130 | 815 |
| 336 | 13/7 14 days I.M. | 900 | | 200 | 3 | 0.1971 | 0.0026 | 0.0920 | 0.0130 | 739 |
| | Fe (100 mcg/dl) | 900 | | 200 | | | | 0.0908 | 0.0120 | |
| 0 | 29 T0 SC | 900 | | 200 | 3 | 0.1945 | 0.0203 | 0.0908 | 0.0120 | 663 |
| 2 | 29 T2 SC | 900 | | 200 | 3 | 0.1557 | 0.0261 | 0.0908 | 0.0120 | 493 |
| 4 | 29 T4 SC | 900 | | 200 | 3 | 0.0867 | 0.0046 | 0.0908 | 0.0120 | 313 |
| 8 | 29 T8 SC | 900 | | 200 | 3 | 0.1109 | 0.0110 | 0.0908 | 0.0120 | 380 |
| 24 | 30 T24 SC | 900 | | 200 | 3 | 0.0908 | 0.0115 | 0.0908 | 0.0120 | 302 |
| 48 | 06/07 48 h SC | 900 | | 200 | 3 | 0.2912 | 0.0158 | 0.0908 | 0.0120 | 1048 |
| 240 | 09/07 10 days SC | 900 | | 200 | 3 | 0.1390 | 0.0279 | 0.0908 | 0.0120 | 423 |
| 336 | 13/7 14 days S.C. | 900 | | 200 | 3 | 0.0865 | 0.0097 | 0.0908 | 0.0120 | 292 |
| | Normal control serum lot 8088 | 900 | | 200 | 1 | 0.1139 | 0.0167 | 0.0908 | 0.0120 | 107 |
| | Pathological ctrl. serum lot 8163 | 900 | | 200 | 1 | 0.1930 | 0.0286 | 0.0908 | 0.0120 | 181 |

(IV.2) Tolerability at the Injection Site.

The complex as per example 1.3 of the invention was also tested—at the same dosage as employed in the pharmacokinetic study (1.67 mg Fe/kg)—for tolerability at the injection site in rats and in hogs. For both types of administration (i.m. bolus and s.c. bolus), the absence of phlogosis and/or necrosis or of other tissutal changes eventually brought about by the injection of the complex of the invention was shown by histological examination of the tissue at the injection site.

(IV.3) Acute Systemic Toxicity.

For the intramuscular administration (i.e. the one which had displayed the higher absorption) further tests were run with the complex according to example I.5 of the invention, in order to study systemic toxicity in rats and in dogs.

Rats.

The doses administered to rats were 5 mg Fe/Kg, 50 mg Fe/kg and 100 mg Fe/kg, respectively, upon 3 administrations within two weeks. In conclusion, it was found that the said multiple intramuscular administrations of Fe(III) maltobionic acid were well tolerated. Observed alterations were very light and were not always dose-correlated in both treated sexes. For the maximum dose, a light increase in platelet, neutrophil and monocyte counts was observed, as well as a light decrease of limphocytes. A light dose-correlated increase of alkaline phosphatase was observed as well.

Dogs.

The doses administered to dogs were 25 mg Fe/Kg and 50 mg Fe/Kg upon three administrations within two weeks. In conclusion, also for dogs, it was found that the said multiple intramuscular administrations of Fe(III) maltobionic acid were well tolerated. The observed alterations for some animals at the highest dose were coloration of the urine and liquid faeces.

The disclosures in Italian Patent Application No. MI2010A001028 from which this application claims priority are incorporated herein by reference.

The invention claimed is:

1. A complex between trivalent iron and maltobionic acid, characterized by a molecular weight Mw between 10,000 and 30,000 Da, by a polydispersity of 1.0-1.8 and by an iron content between 25% and 40% by weight.

2. The complex according to claim 1, characterized by a polydispersity of 1.0-1.6.

3. The complex according to claim 1, characterized by a molecular weight Mw between 12,000 and 27,000 Da, by a polydispersity of 1.1-1.5 and by an iron content between 25% and 40% by weight.

4. The complex according to claim 3, characterized by a molecular weight Mw between 13,000 and 18,000 Da, by a polydispersity of 1.2-1.4 and by an iron content between 25% and 40% by weight.

5. The complex according to claim 4, characterized by a molecular weight Mw between 13,000 and 18,000 Da, by a polydispersity of 1.2-1.4 and by an iron content between 25% and 35% by weight.

6. The complex according to claim 3, characterized by a molecular weight Mw between 12,000 and 27,000 Da, by a polydispersity of 1.1-1.5 and by an iron content between 26% and 32% by weight.

7. The complex according to claim 5, characterized by a molecular weight Mw between 13,000 and 18,000 Da, by a polydispersity of 1.2-1.4 and by an iron content between 26.5% and 28.5% by weight.

8. The complex according to claim 1, wherein the trivalent iron is in the form of ferric oxide-hydroxide.

9. The complex according to claim 1 for use as a medicament in intramuscular or subcutaneous administration in the treatment of anemic states of mammals.

10. A method for the treatment of anemic states in mammals comprising the step of injecting intramuscularly or subcutaneously to the mammals a pharmaceutical solution comprising a complex according to claim 1.

11. A method for the treatment of anemic states in human beings comprising the step of injecting intramuscularly or subcutaneously to the human beings a pharmaceutical solution comprising a complex according to claim 1.

12. A pharmaceutical preparation for intramuscular or subcutaneous administration to mammals, comprising a complex according to claim 1.

13. The pharmaceutical preparation according to claim 12 for intramuscular bolus injection or for subcutaneous bolus injection to mammals.

14. The pharmaceutical preparation according to claim 13 for intramuscular bolus injection or for subcutaneous bolus injection to human beings.

15. The pharmaceutical preparation according to claim 12, comprising at least one pharmaceutically acceptable excipient.

16. The pharmaceutical preparation according to claim 12, comprising up to 200 mg/ml of trivalent iron.

17. The pharmaceutical preparation according to claim 16, comprising 80-120 mg/ml of trivalent iron.

18. The pharmaceutical preparation according to claim 12, having a pH comprised between 6.0 and 8.0.

* * * * *